United States Patent
Pratt et al.

(10) Patent No.: US 11,131,613 B2
(45) Date of Patent: Sep. 28, 2021

(54) SYSTEMS AND METHODS FOR HANDHELD SNOW STABILITY ANALYZER

(71) Applicant: Avametrix, LLC, Boise, ID (US)

(72) Inventors: Gordon D. Pratt, Boise, ID (US); Nicole D. Rota, Tamarack, ID (US)

(*) Notice: Subject to any disclaimer, the term of this patent is extended or adjusted under 35 U.S.C. 154(b) by 0 days.

(21) Appl. No.: 16/685,808

(22) Filed: Nov. 15, 2019

(65) Prior Publication Data

US 2020/0158609 A1 May 21, 2020

Related U.S. Application Data

(60) Provisional application No. 62/765,822, filed on Sep. 17, 2018.

(51) Int. Cl.
| | |
|---|---|
| *G01N 9/24* | (2006.01) |
| *G01N 33/18* | (2006.01) |
| *G01S 7/06* | (2006.01) |
| *G01S 13/88* | (2006.01) |
| *G08B 21/10* | (2006.01) |
| *G01S 13/42* | (2006.01) |

(52) U.S. Cl.
CPC ............... *G01N 9/24* (2013.01); *G01N 33/18* (2013.01); *G01S 7/06* (2013.01); *G01S 13/42* (2013.01); *G01S 13/886* (2013.01); *G08B 21/10* (2013.01); *G01N 2033/1873* (2013.01)

(58) Field of Classification Search
CPC .. G01N 9/24; G01N 33/18; G01N 2033/1873; G01S 7/06; G01S 13/886; G01S 13/42; G08B 21/10
USPC ........... 73/32 R, 596–602, 78, 290 R, 290 V, 73/865.8, 866, 170.21, 170.26, 170.28, 73/170.16, 861, 861.81, 861.85; 374/100, 374/117, 118, 141, 142, 208; 340/901, 340/902, 904, 540, 601
See application file for complete search history.

(56) References Cited

U.S. PATENT DOCUMENTS

| | | | | |
|---|---|---|---|---|
| 6,957,593 | B1 * | 10/2005 | Burns | G01N 29/11 73/866 |
| 2008/0159079 | A1 * | 7/2008 | Dir | A01M 31/004 367/139 |
| 2010/0128863 | A1 * | 5/2010 | Krum | H04M 1/663 379/207.02 |
| 2013/0204532 | A1 * | 8/2013 | Nystrom | H04R 5/033 702/3 |
| 2014/0116127 | A1 * | 5/2014 | Christian | G01N 33/18 73/170.17 |
| 2015/0134288 | A1 * | 5/2015 | Kurrant | G01S 13/885 702/85 |
| 2016/0310065 | A1 * | 10/2016 | Arif | A61B 5/1118 |
| 2017/0003176 | A1 * | 1/2017 | Phan Le | G01N 29/032 |

FOREIGN PATENT DOCUMENTS

WO    WO2020071919 A1    4/2020

* cited by examiner

*Primary Examiner* — Robert R Raevis
(74) *Attorney, Agent, or Firm* — Parsons Behle & Latimer

(57) ABSTRACT

A compact, handheld, battery-powered radar transceiver used to analyze the stability of the snowpack to avoid avalanche danger. The device scans the snowpack and presents a depth vs. density profile chart and highlights layers of concern (strong over weak layers) and other relevant information on an integrated backlit touchscreen LCD.

12 Claims, 8 Drawing Sheets

SYSTEMS AND METHODS FOR HANDHELD SNOW STABILITY ANALYZER

CROSS-REFERENCE TO RELATED APPLICATIONS

This application, under 35 U.S.C. § 119, claims the benefit of U.S. Provisional Patent Application Ser. No. 62/765,822 filed on Sep. 17, 2018, and entitled "Compact Handheld Snowpack Analyzer," the contents of which are hereby incorporated by reference herein.

FIELD OF THE DISCLOSURE

This disclosure relates generally to snowpack stability analysis. In particular, systems and methods for a handheld snowpack stability analyzer are disclosed.

BACKGROUND

Every year, over 150 people are killed in avalanches. Countless more are injured or get lucky and are only partially buried and can escape. It is estimated that humans trigger 90 percent of avalanche disasters. Most are climbers, skiers, snowboarders, snowmobilers, snow shoe trekkers, hikers, hunters, or other "backcountry" enthusiasts. As used herein, "backcountry" means a geographical area that is remote, undeveloped, isolated, or difficult to access.

Typically, an avalanche, or snow slide, is caused by a combination of terrain, snowpack, and weather conditions. Disastrous and potentially fatal avalanches occur when massive slabs of snow break loose from a mountainside. These hazards can travel up to 100 miles per hour down the mountainside carrying many tons of snow, ice, and debris along with them.

Snow slides can start on mountain slopes with as little as a 30-degree incline, but they occur most frequently on slopes of 35-50 degrees. Avalanches are most common during the winter, Dec. to Apr. in the Northern Hemisphere, but they do occur year-round.

Typically, all dry snow avalanches are the result of three conditions: an unstable strong (hard) layer over a weak (soft) layer, a slope (generally between 32° and 45°), and a trigger. The highest risk period is during and immediately after a snow storm. Underlying snowpack, overloaded by a quick deluge of snow, can cause a weak layer beneath the slab to fracture naturally, or by a human trigger.

Human-triggered avalanches often start when somebody walks or rides over a slab with an underlying weak layer. The weak layer collapses, causing the overlaying mass of snow to fracture and start to slide.

Currently, the way to assess a particular snowpack for avalanche hazard requires hand-digging a snow pit to look at the relative hardness of different snow layers that formed during a season. This is time consuming and difficult. Other drawbacks, inconveniences, and issues with existing avalanche condition analysis systems also exist.

SUMMARY

Accordingly, disclosed embodiments address the above and other drawbacks, inconveniences, and issues with existing avalanche condition analysis systems and methods.

Disclosed embodiments include a handheld snowpack analyzer having a housing, an impulse radar chipset in communication with an antenna, a display, and at least one hardware processor programmed to perform a predefined set of operations at least a portion of which are stored in at least one memory, the predefined set of operations including operating the impulse radar chipset and antenna to perform a radar scan and collect radar scan data for a portion of a snowpack, analyze the radar scan data to create a profile of snow depth and hardness, and displaying the profile on the display.

Further disclosed embodiments include a position detection circuit that determines a current location on the Earth and stores the current location with the profile of snow depth and hardness. In some embodiments, the position detection circuit is a Global Positioning System (GPS).

Further disclosed embodiments include an inclinometer that determines an inclination of a longitudinal axis of the handheld snowpack analyzer.

Further disclosed embodiments include a compass that determines a compass direction of a longitudinal axis of the handheld snowpack analyzer.

Disclosed embodiments also include a snowpack analysis engine that converts the dielectric constant of snow layers to density, which is then converted to the logarithmic hand hardness scale.

Further disclosed embodiments include a short distance radio frequency transceiver that receives data comprising ambient temperature or wind speed. In some embodiments, the data comprising ambient temperature or wind speed is transmitted from a fob separate from the handheld snowpack analyzer.

Also disclosed is a snowpack analyzer for mounting on a vehicle, the analyzer having an impulse radar chipset in communication with an antenna, a display, and at least one hardware processor programmed to perform a predefined set of operations at least a portion of which are stored in at least one memory, the predefined set of operations including operating the impulse radar chipset and antenna to perform a radar scan and collect radar scan data for a portion of a snowpack, analyze the radar scan data to create a profile of snow depth and hardness, and displaying the profile on the display.

In some embodiments, the vehicle is an unmanned remotely pilotable aircraft. In further disclosed embodiments, the vehicle is a snowmachine and the analyzer also includes an alarm to indicate a potential avalanche condition.

Also disclosed is an environmental detector fob having an ambient temperature detector, a wind speed detector, and a radio transceiver. In some embodiments, the ambient temperature detector is a thermistor.

In further disclosed embodiments, the wind speed detector is a microphone and the wind speed is derived from wind noise detected with the microphone.

In further disclosed embodiments, the radio transceiver is a short-range radio transceiver. In still further disclosed embodiments, the fob includes at least one push button to activate the radio transceiver.

In further disclosed embodiments, the fob includes at least one attachment clip for attaching the fob to a wearer.

Other embodiments, features, and configurations are also disclosed.

Figure 1:
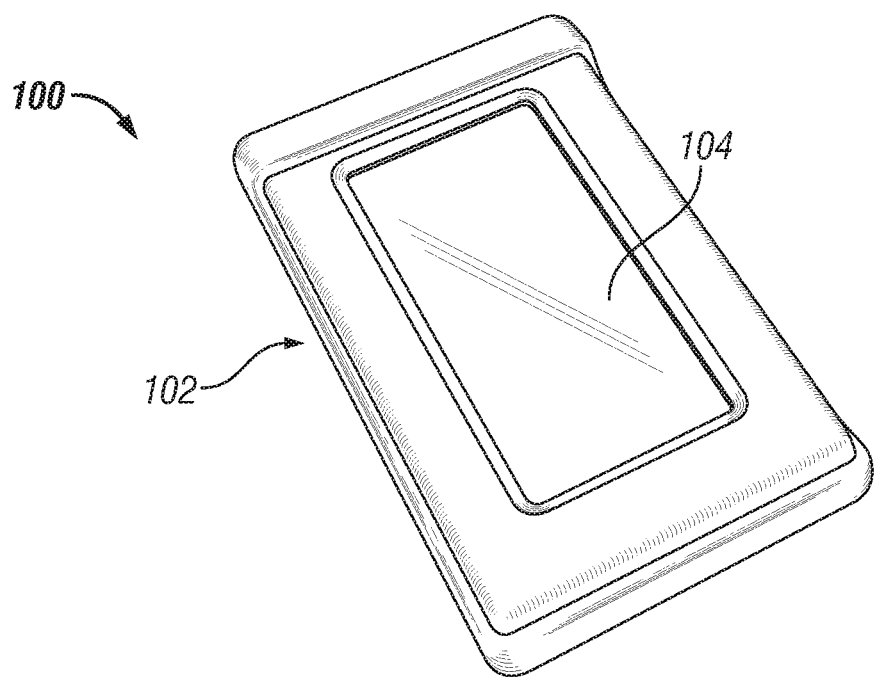
FIG. 1 is a perspective view of a handheld snowpack analyzer in accordance with disclosed embodiments.

While the disclosure is susceptible to various modifications and alternative forms, specific embodiments have been shown by way of example in the drawings and will be described in detail herein. However, it should be understood that the disclosure is not intended to be limited to the particular forms disclosed. Rather, the intention is to cover all modifications, equivalents and alternatives falling within the spirit and scope of the invention as defined by the appended claims.

DETAILED DESCRIPTION

It should also be understood that, as used herein, the terms "vertical," "horizontal," "lateral," "upper," "lower," "left," "right," "inner," "outer," etc., can refer to relative directions or positions of features in the disclosed devices and/or assemblies shown in the Figures. For example, "upper" or "uppermost" can refer to a feature positioned closer to the top of a page than another feature. These terms, however, should be construed broadly to include devices and/or assemblies having other orientations, such as inverted or inclined orientations where top/bottom, over/under, above/below, up/down, and left/right can be interchanged depending on the orientation.

FIG. 1 is a perspective view of a handheld snowpack analyzer 100 in accordance with disclosed embodiments. As used herein "handheld" means capable of being held by a typical human hand. Generally, embodiments of the handheld snowpack analyzer 100 are approximately 130 mm along a longitudinal axis (top-bottom), 82 mm along a latitudinal axis (left-right), and 25 mm along a vertical axis (front-back) and weigh approximately 225 g (~8 oz) or less. Other sizes and weights are also possible.

As also indicated handheld snowpack analyzer 100 includes a suitable housing 102 and a display 104. Housing 102 may be a multi-part assembly (see, e.g., FIG. 2) and is designed to withstand environmental conditions that may occur in backcountry regions. For example, the housing 102, or parts of housing 102, may be flame-resistant, high-impact, injection molded plastic, silicone, rubber, or the like, and housing 102 may be water-proof or water-resistant, may be able to allow operation from sea-level to 30,000 feet in altitude, may be able to withstand ambient temperatures from −40° C. to 70° C., may be drop and shock resistant, and may be brightly colored (e.g., high contrast) to be easily locatable if dropped in the snow. Other configurations are also possible.

Display 104 is suitable touch-screen that displays information and accepts touch and gesture input as disclosed herein. For example, display 104 may be a 240×128 pixel transflective chip-on-glass LCD with resistive touchscreen and LED backlight. The LCD provides suitable visibility in most outdoor and indoor lighting conditions. Other displays 104 and touch detection types may also be used.

Figure 2:
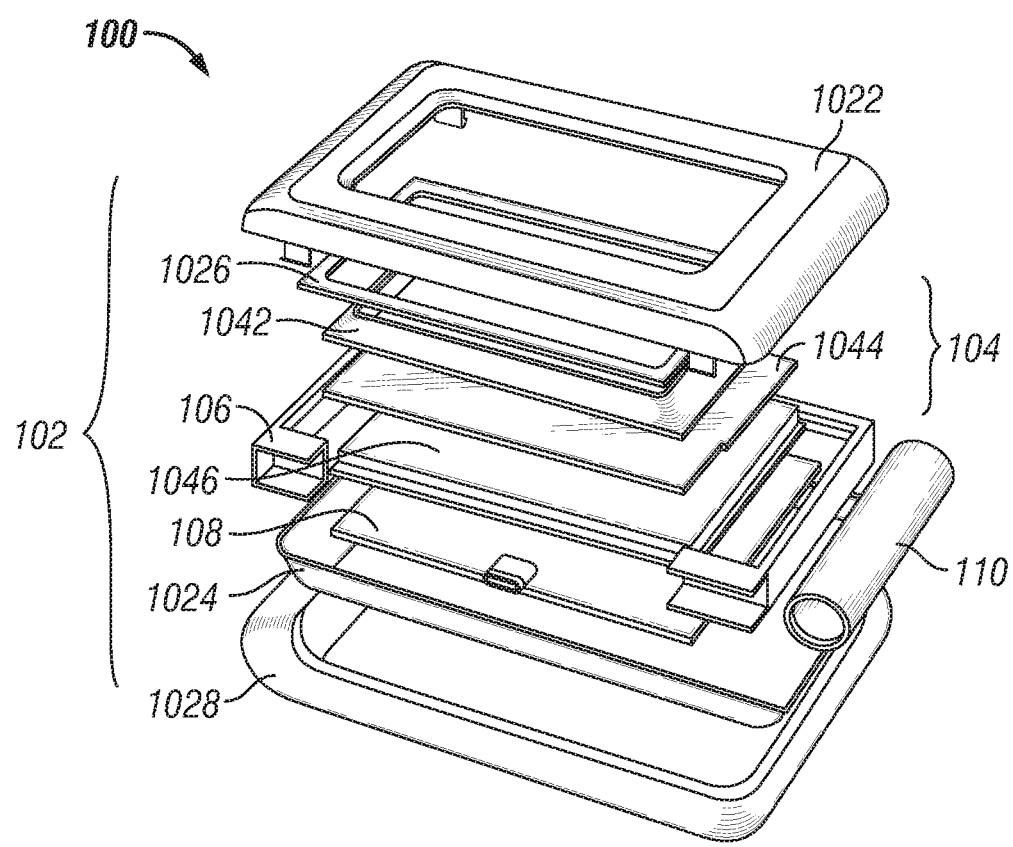
FIG. 2 is an exploded perspective view of a handheld snowpack analyzer in accordance with disclosed embodiments.

FIG. 2 is an exploded perspective view of a handheld snowpack analyzer 100 in accordance with disclosed embodiments. As shown in FIG. 2, multi-part housing 102 may include a top enclosure 1022 and a bottom enclosure 1024 made of water-resistant or water-proof molded plastic or the like joined with a permanent snap fit, mechanical fastener, or the like. A sealing gasket 1026 made of silicone, rubber, or the like may be used to additionally seal the housing 104 and display 104 from environmental elements. As also shown, the housing 102 may be further protected by a molded silicone sleeve 1028 or the like.

As also shown in FIG. 2, display 104 may include a touchpanel 1042, an LCD screen 1044, and a LED backlight 1046. Other display 104 types (e.g., OLED, AMOLED, Super AMOLED, TFT, IPS, TFT-LCD, ePaper, or the like), with other component parts, are also possible.

As also shown in FIG. 2, handheld snowpack analyzer 100 may also include a support chassis 106 or the like to hold components, such as PCB 108 and power source 110, securely within the housing 102. Power source 110 may be any suitable power source. For example, some embodiments of handheld snowpack analyzer 100 may be powered by one rechargeable lithium-ion or nickel metal hydride battery providing a DC voltage of 3.0-3.6 VDC, a maximum average power consumption of less than 250 mW, sized to provide a minimum time between charges of approximately 10 hours, including at least 50 scans, and may be recharged in six hours or less through a port (not shown in FIGS. 1-2) such as a USB-C port. Other ports with suitable environmental protections (e.g., covers) may also be provided, such as SD, MicroSD, or other non-volatile memory slots, or the like, may also be included.

Figure 3:
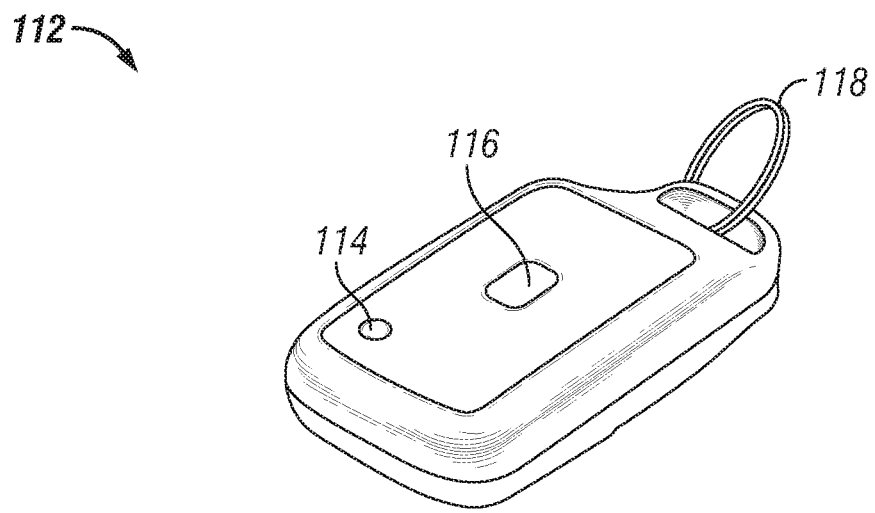
FIG. 3 is a perspective view of a fob containing some additional elements of the snowpack analyzer system in accordance with disclosed embodiments.

FIG. 3 is a perspective view of a fob 112 containing some additional elements of the snowpack analyzer system in accordance with disclosed embodiments. In some embodiments of handheld snowpack analyzer 100, a separate fob 112 may contain a thermistor (not visible, but encased in fob 112), a microphone 114, and at least one push button 116 to activate a short-range radio transceiver (e.g., Bluetooth®) for the sensors on the fob 112 to transmit ambient temperature and wind-noise level to the handheld snowpack analyzer 100. The wind speed may be derived from wind noise detected with the microphone 114. Fob 112 may also include other sensors (e.g., barometers, pressure, etc.) and user-replaceable battery. As also indicated, the fob 112 may be attached to a coat zipper, backpack, or the like, with a split ring 118 or other suitable clip, carabiner, or the like.

As disclosed above, for embodiments of the handheld snowpack analyzer 100 could be used to locate a buried victim or equipment using microwave radar more quickly than the conventional method of probing, after being located from the surface using an avalanche transceiver beacon or the like.

Figure 4:
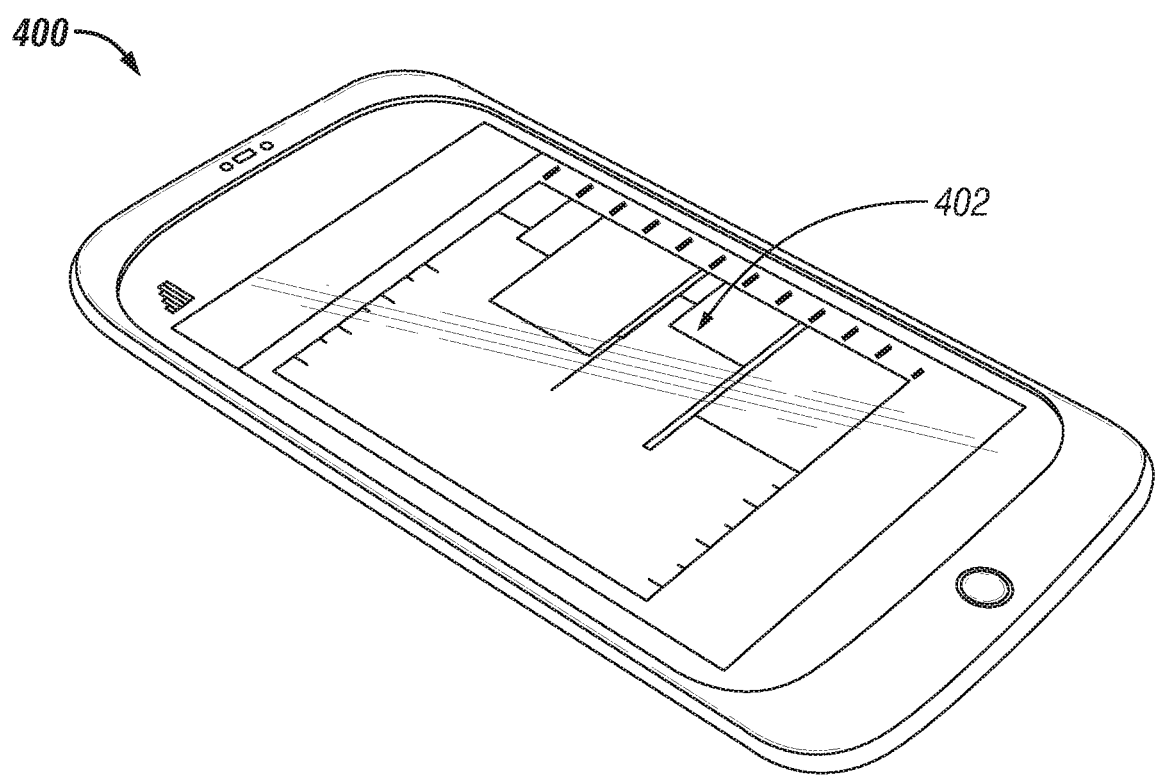
FIG. 4 is a perspective view of a smartphone running an application ("app") in accordance with disclosed embodiments.

FIG. 4 is a perspective view of a smartphone 400 running an application 402 ("app") in accordance with disclosed embodiments. The handheld snowpack analyzer 100 can interface (e.g., via a USB-C cable, a wireless connection, or the like) to a smartphone 400 running on any operating system platform (e.g., Android, iOS, or the like). The app 402 features a simple and intuitive interface which allows the user to review, share, or upload profiles to a website, set preferences for analyzer 100 operation, or the like.

Figure 5:
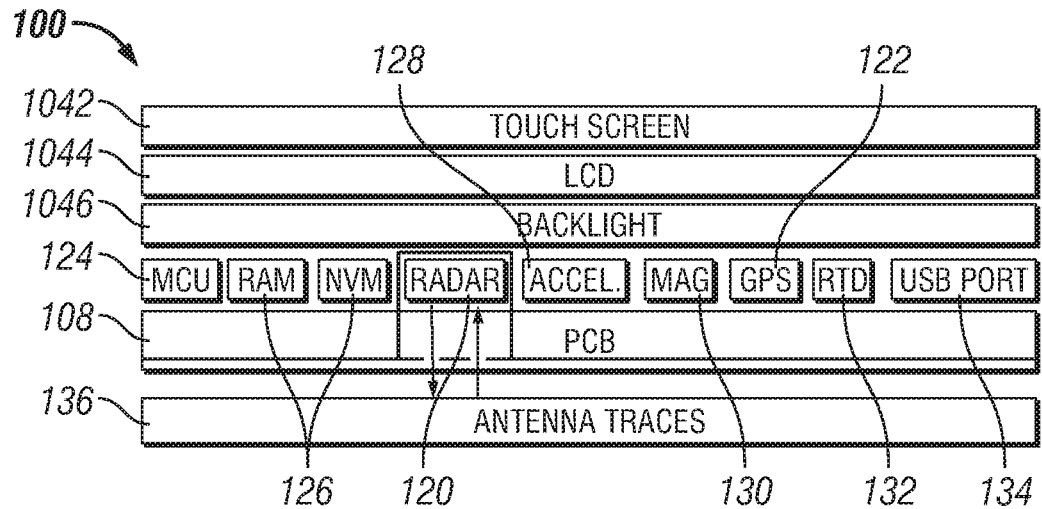
FIG. 5 is a schematic cross-sectional view of a handheld snowpack analyzer 100 in accordance with disclosed embodiments.

FIG. 5 is a schematic cross-sectional view of a handheld snowpack analyzer 100 in accordance with disclosed embodiments. As illustrated schematically, PCB 108 includes an impulse radar chip set 120, a position detection circuit (e.g., GPS 122 with its own integrated antenna), a hardware processor 124 (e.g., micro-controller unit), memory 126 (e.g., random access memory and/or non-volatile memory), an inclinometer or accelerometer 128, a compass or magnetometer 130, a thermistor or other resistive temperature device 132, a port 134, and other digital components on one side of PCB 108 and a trace-only RF antenna or antenna array 136 on the other. As also shown schematically a ground plane or RF shielding 138 may separate the RF antenna or antenna array 136 from the other PCB 108 components.

Impulse radar chipset 120 may be any suitable radar chipset. For example, some embodiments may use a XeThru X4 or equivalent chipset. By way of further example, the X4 UWB Impulse Radar Transceiver System-on-Chip (SoC) combines a 7.29/8.748 GHz transmitter for unlicensed operation in worldwide markets, a direct RF-sampling receiver, a fully programmable system controller, and advanced power management functions in a single chipset 120 and can operate in either 7.29 GHz or 8.748 GHz for unlicensed operation in worldwide markets, transmit pulse power less than −7.3 dBm and 10 cm range resolution from pulse waveform, has low power consumption, typically <120 mW, has an operating temperature range −40 to +85° C., has advanced power management enabling low power duty cycle controlled operation, has bi-phase coding of transmitted pulses for spectrum spreading, has ultra-high spatial resolution for simultaneous multi-object tracking, has a master/slave Serial Peripheral Interface (SPI), and occupies a compact WLCSP, 0.4 mm pitch, 48 pin package. The above-noted features are merely exemplary and other impulse radar chipset 120 may also be used.

Figure 6:
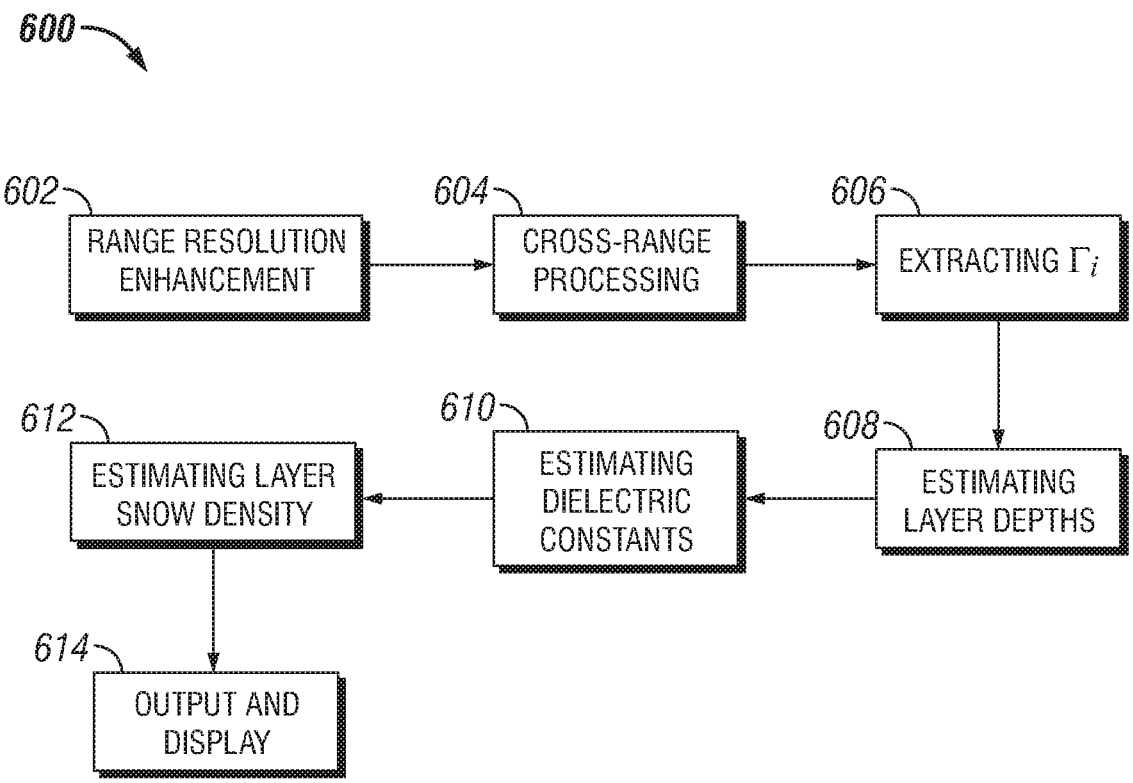
FIG. 6 is a schematic flowchart illustrating radar processing in accordance with disclosed embodiments.

FIG. 6 is a schematic flowchart illustrating radar processing 600 in accordance with disclosed embodiments. As shown at 602 range resolution enhancement may include increasing range sampling. At 604 cross-range processing may include processing overlapping of multiple antenna scans. At 606 $\Gamma_i$ is extracted based on the measurement range profiles and their transition among range bins. At 608 layer depths are estimated by extracting the range bins with identical scanning properties. At 610 dielectric constants are estimated by using a basic neural network machine learning algorithm that corrects the layer combinations with different dielectric properties with the range profile. At 612 the snow layer density is estimated by using empirical equations relating dielectric constants with material densities. At 614 the profile is output and displayed (e.g., on display 104).

As will be apparent to those of ordinary skill in the art having the benefit of this disclosure, the disclosed handheld snowpack analyzer 100 is a compact, handheld, battery-powered radar transceiver used to analyze the stability of the snowpack to predict and avoid avalanche danger. The device scans the snowpack and presents a depth vs. density profile chart and highlights layers of concern (strong layers over weak layers) and other relevant information on an integrated backlit touchscreen LCD.

As also will be apparent to those of ordinary skill in the art having the benefit of this disclosure, analyzer 100 includes a processor 124 and memory 126 in communication with the processor 124. The processor 124 is configured to execute instructions stored on the memory 126 which cause the processor 124 to receive the sensor data (e.g., from radar chip set 120, position circuit (GPS 122), accelerometer/inclinometer 128, compass/magnetometer 130, thermistor/RTD 132, and the like). The instructions also cause the processor to calculate profiles and other displays based on the received data as disclosed herein. The processor 124 performs computations using a central processing unit (CPU), a graphical processing unit (GPU), a digital signal processor (DSP), a peripheral interface controller (PIC), or another type of microprocessor. It may be implemented as an integrated circuit, a field programmable gate array (FPGA), an application specific integrated circuit (ASIC), a combination of logic gate circuitry, other types of digital or analog electrical design components, or the like, or combinations thereof.

As also will be apparent to those of ordinary skill in the art having the benefit of this disclosure, analyzer 100 includes a touchpanel 1042 for a user to input, select, and otherwise operate the analyzer 100 by using touches and gestures (e.g., taps, directional swipes, multi-touches, pinches, expansions, etc.).

Figure 7:
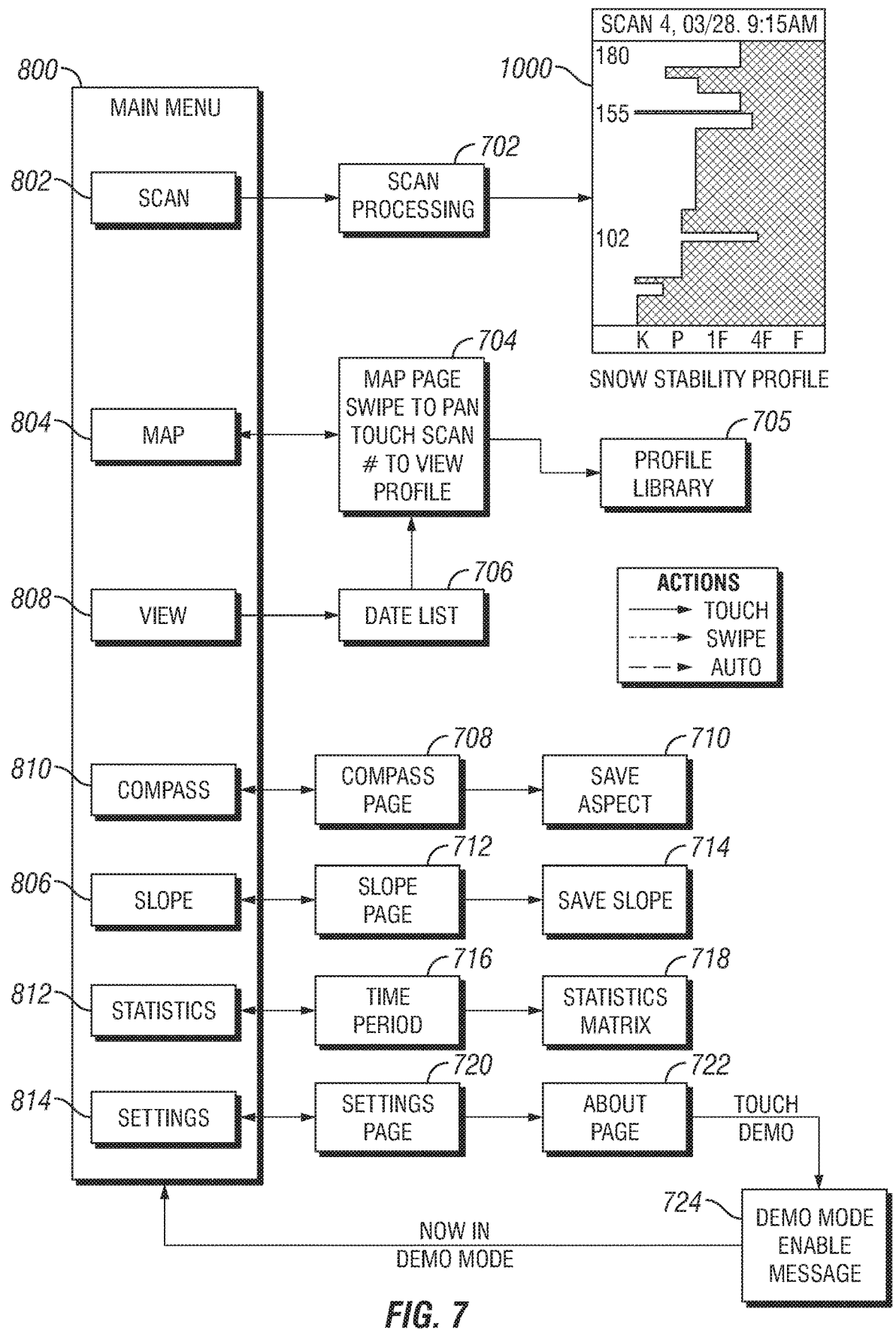
FIG. 7 is a schematic flowchart illustrating potential operations and other processor instructions in accordance with disclosed embodiments.

FIG. 7 is a schematic flowchart illustrating potential operations and other processor instructions 700 in accordance with disclosed embodiments. As a person of ordinary skill in the art having the benefit of this disclosure would understand, the analyzer 100 includes a processor and memory in communication with the processor. The processor is configured to execute instructions stored on the memory which cause the processor to receive the data from the various sensors. The instructions also cause the processor to calculate snowpack data based on the sensor data.

As shown in FIG. 7, after power-on, the main menu 800 provides touch buttons (802, 804, 806, 808, 810, 812, 814) to invoke most major functions, and may show local time, temperature, wind, and elevation in various units, and a settings icon 814. Touching a button activates the associated function. Returning to the main menu may be accomplished with a double touch or a "home" menu button (not shown in FIG. 7). As also shown, touching scan icon 802 invokes a snowpack analysis engine 702 that causes processor (e.g., processor 124) to perform the instructions stored in memory (e.g., memory 126) to operate the impulse radar chipset 120 and antenna 136 to perform a radar scan and collect radar scan data for a portion of a snowpack, analyze the radar scan data to create a profile (e.g., profile 1000 or 1100) of snow depth and hardness, and display the profile (e.g., profile 1000 or 1100) on the display 104. The profile (e.g., profile 1000 or 1100) is also stored in a profile library 705 in memory (e.g., memory 126).

Other instructions and associated functions 700 include map page 704 that operates GPS 122, or other position detection circuit (e.g., cellular), to among other things display a map and location on Earth of the analyzer 100 and the locations of the previously stored scans (as discussed below in connection with FIG. 13). Date list 706 may collect current time and date information (e.g., from GPS 122), display the same (e.g., FIG. 8 at 814 and FIG. 12 at 1202), and store the same for scans stored in profile library 705. Compass page 708 invokes operation of the compass functions (e.g., compass or magnetometer 130) such as headings or aspect data (e.g., North, South, East, West and/or latitude and longitude coordinates) and as indicated at 710 may save the same for later use and display (e.g., FIG. 12). Slope page 712 invokes operation of incline functions (e.g., inclinometer or accelerometer 128) and measures the degree of slope and as indicated at 714 may save the same for later use or display (e.g., FIG. 12). Time period 718 invokes clock functions and keeps track of, among other things, the time a scan is taken and stores the same in a statistics matrix 718. Other functions such as settings page 720, about page 722, and demonstration mode 724 may also be included. As one of ordinary skill in the art having the benefit of this disclosure would understand, other instructions and functions 700 may also be included.

Figure 8:
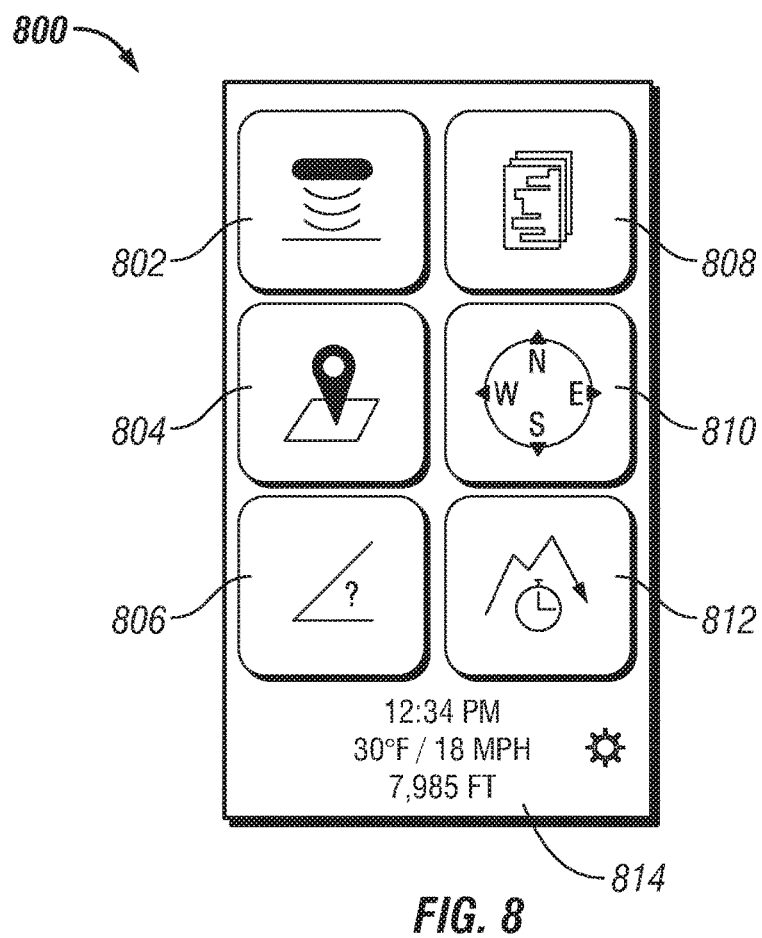
FIG. 8 is an exemplary display of a main menu 800 as it appears on display 104 in accordance with disclosed embodiments.

FIG. 8 is an exemplary display of a main menu 800 as it appears on display 104 in accordance with disclosed embodiments. As shown, a number of icons are shown (802, 804, 806, 808, 810, 812, 814) that correspond to various displays and operations for the analyzer 100. The icons and arrangement shown in FIG. 8 are merely exemplary and other arrangements, icons, text, pictures, or the like may also be used. As shown, scan icon 802 will invoke the snowpack scanning functions and display as described herein, map icon 804 invokes the map functions and displays, slope angle icon 806 invokes the slope measuring functions and displays, view icon 808 invokes other views as described herein, compass icon 810 invokes the compass functions and displays, statistics icon 812 invokes stored data and displays, and information icon 814 invokes device setting functions and display preferences for time, date, elevation, temperature, wind speed, and other general information as desired. Other functions and displays are also possible.

Figure 9A:
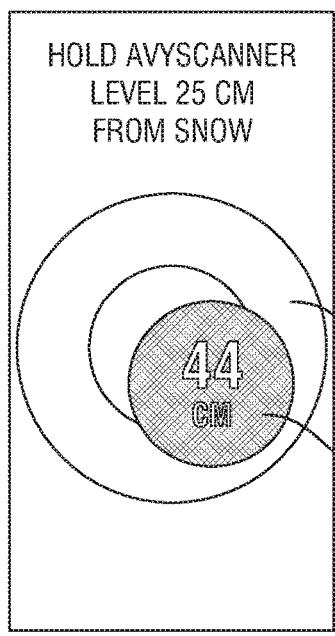
FIGS. 9A-9B are exemplary displays of a scan function 802 as it appears on display 104 in accordance with disclosed embodiments.
Figure 9B:
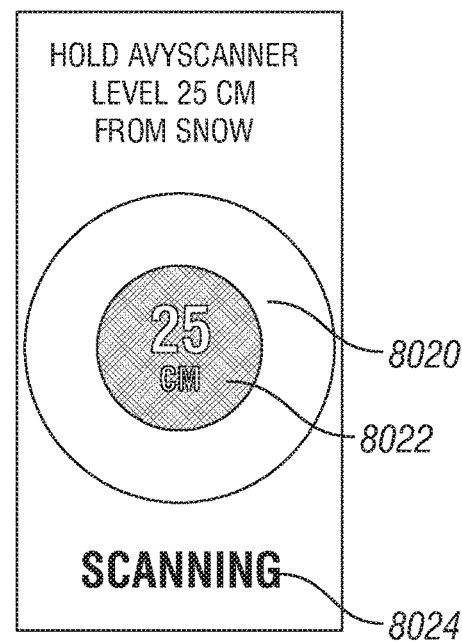

FIGS. 9A-9B are exemplary displays of a scan function 802 as it appears on display 104 in accordance with disclosed embodiments. When a user touches on the scan icon 802 the display 104 shows instructions to "Hold AvyScanner level XX cm (or inches) from snow" as shown in FIG. 9A. The units specified of cm or inches may be set by the user on settings page 814. The distance from the snow that is display may depend on the particular radar antenna 138 configuration. In some embodiments, it may be preferable to place the unit directly on the top surface of the snow in which case display 104 may show an instruction to "Place AvyScanner on top of snow," or the like.

In some embodiments, a level cue 8020 (e.g., a "bubble level" icon) and distance cue 8022 (radar-measured distance to snow) may be displayed that prompts the user to hold the device level using an animated bubble level icon and displays a digital readout of distance to the snow surface. When the level and distance requirements are both met within a predetermined tolerance, analyzer 100 will initiate the radar scan sequence and, if the scan takes more than 1 second, present a laterally moving dot, hourglass, flashing text, or equivalent animation as indicated at 8024 while the scan is in progress.

Figure 10:
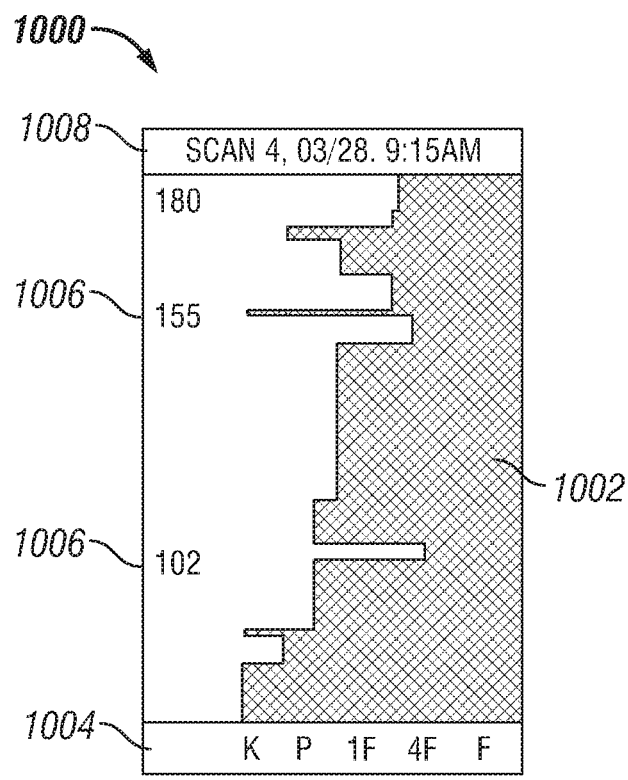
FIG. 10 is an exemplary profile display in accordance with disclosed embodiments.
Figure 11:
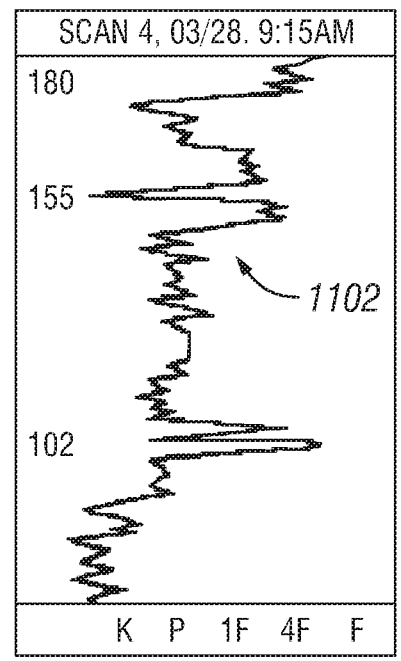
FIG. 11 is an exemplary hi-fidelity profile display in accordance with disclosed embodiments.

When the scan sequence is complete, if processing takes more than 1 second, the device may also indicate "Processing Profile" and the "Wait" hourglass icon at 8024 until the profile is displayed (as shown in FIGS. 10-11).

The raw radar scan data is processed into a Profile Data Packet (PDP) that indicates the depth and hardness of the snowpack along with other relevant information. As used herein a PDP is an ASCII or other text string of all the detected parameters of the profile scan that allows the scan data to be stored in a compact manner while enabling the analyzer 100, app 402, or other system, to recreate a profile and associated images in any possible format. In some embodiments, the analyzer 100 may save the PDPs in FIFO order to memory 126 (e.g., non-volatile memory) in a comma-delimited ASCII text format. Other formats may also be used. The PDP file is also used to produce the Profile and Detail pages for review and can be uploaded to the SmartPhone app 402.

The PDP information saved in memory 126 with each scan may include: 1. Scan date and time, 2. Latitude/Longitude, 3. Elevation in feet or meters, 4. Outside Air Temperature, 5. Snow depth (surface to ground) or deepest layer, 6. Slope angle in degrees, 7. Number of layers, 8. Slope aspect, 9. Depth/density for as many layers as detected, 10. A snow crystal type, and 11. Checksum to verify PDP file integrity. Other information may also be included in the PDP.

In some embodiments, scans for the current day may be displayed in a matrix or "nested" format that are accessed by various touches, swipes, or gestures. For example, after a scan a profile (e.g., FIG. 10) may be first displayed on display 104. A swipe up may change display to a high-fidelity profile (e.g., FIG. 11) (and vice versa—swipe down from high-fidelity to first profile), another swipe up may display details for that profile (e.g., FIG. 12), another swipe may display a map showing locations of the scan (e.g., FIG. 13), and a double tap may exit to main menu 800. Other sequences and types of display are also possible.

FIG. 10 is an exemplary profile display in accordance with disclosed embodiments. As shown, a conventional snow pit profile (cross section) 1000 may be displayed from the saved PDP data packet with depth on the vertical axis 1002 up to 200 cm of depth scaled automatically to the full height of the available vertical display area, with the snow surface at the top. Hardness may be displayed on the horizontal axis 1004 indexed to the logarithmic Hand Hardness Test (HHT) scale: first (softest snow), Four Fingers, One Finger, Pencil, Knife (hardest hardest) as follows (from right to left): F 4F 1F P K. HHT value for each layer may be indexed to ⅓ step increments: F−(~40 Kg/m$^3$), F, F+, 4F−, 4F, 4F+, 1F−, 1F, 1F+, P−, P, P+, K−, K. K+ and Ice (>900 kg/m$^3$). The depth, in centimeters or inches, may be displayed on the left edge of the display for Layers of Concern 1006 (any harder layer over softer layer that exceeds one full step on the HHT scale). The scan number of the day, the date, and the time (in the format specified on the Settings Page) may be displayed in the upper left corner 1008 of the Profile page 1000.

FIG. 11 is an exemplary high-fidelity profile display 1100 in accordance with disclosed embodiments. As shown, The high-fidelity profile 1100 may display the depth/density profile in a curvilinear format 1102 using the raw values from the algorithm for each depth recorded, rather than indexed.

Figure 12:
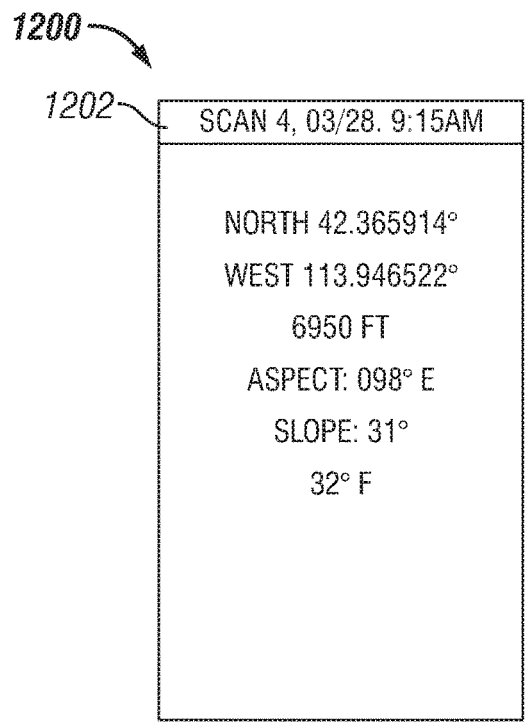
FIG. 12 is an exemplary detail display in accordance with disclosed embodiments.

FIG. 12 is an exemplary detail display 1200 in accordance with disclosed embodiments. As indicated, the details display 1200 may display LAT/LON, ELEVATION, ASPECT, SLOPE, TEMP, or more data as text for the current scan (in units specified on Settings Page). The scan number of the day and time may be displayed in the upper left corner of the details display 1200.

Figure 13:
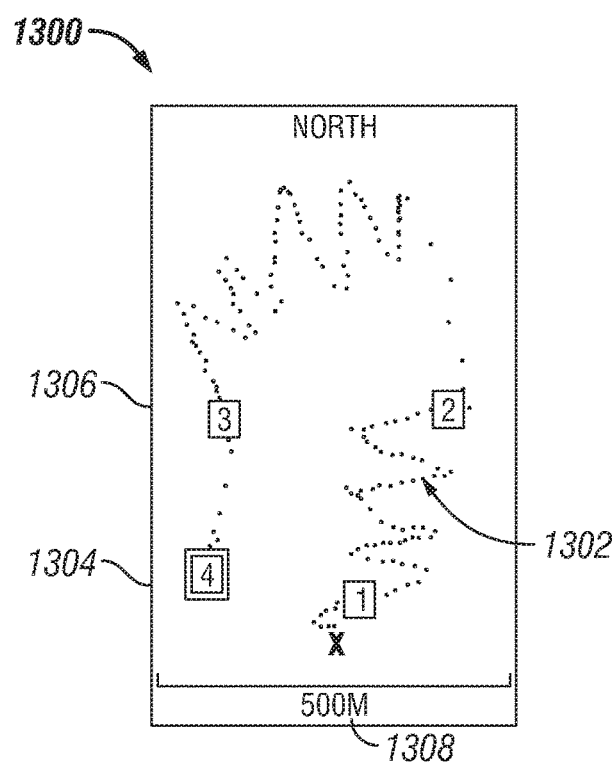
FIG. 13 is an exemplary scan location display in accordance with disclosed embodiments.

FIG. 13 is an exemplary scan location display 1300 in accordance with disclosed embodiments. As shown, the scan location display 1300 may display a portion of the map 1302 scaled to show the current scan location 1304 (e.g., double or highlighted box around scan 4 indicating the current scan) relative to the route 1306 (dotted line) and other scans (single or non-highlighted boxes 1-3). Scale may be indicated on the width of the display 1308 in the units set in the settings.

As will be apparent to those of ordinary skill in the art having the benefit of this disclosure, and with particular reference to FIG. 8, analyzer 100 also includes a compass 810 function that gives heading and compass directions, and inclinometer (or accelerometer) 806 that gives slope angles, mapping display 804, and statistical or historic data about usage, routes, profiles, and the like. Other typical GPS and mapping features may also be included in analyzer 100.

Figure 14:
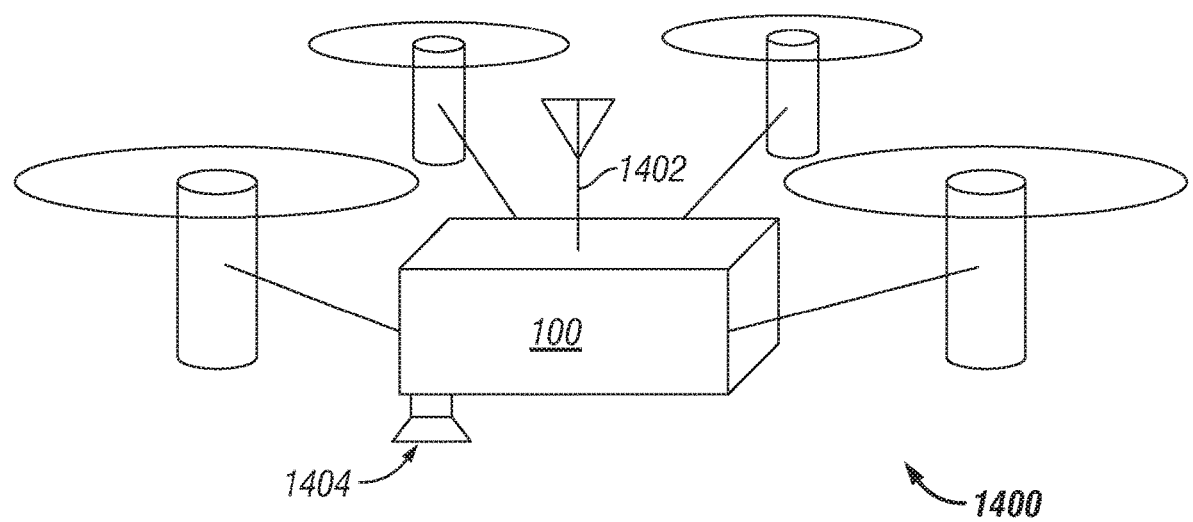
FIG. 14 is a schematic illustration of a vehicle-mounted snowpack analyzer 100 in accordance with disclosed embodiments.

FIG. 14 is a schematic illustration of a vehicle-mounted snowpack analyzer 100 in accordance with disclosed embodiments. As shown, a vehicle 1400, in some embodiments a drone (i.e., remote controlled unmanned flying craft), can have a snowpack analyzer 100 attached and communicate back to the remote pilot via radio or other antenna 1402. In this manner, a number of analyzers 100 may be remotely and safely piloted to backcountry or other locations to evaluate snowpack conditions. Analyzer 100 may communicate in real, or near-real, time with the operator via antenna 1402, or may store profiles (e.g., 1000, 1100) for later viewing and evaluation upon return of the vehicle 1400 to the operator's location. In this manner, slopes may be evaluated without putting people at risk.

In other embodiments, vehicle 1400 may comprise a snowmachine, snowmobile, motorized sled, snow bike, or the like with an appropriate mount for the analyzer 100. For such embodiments, analyzer 100 may be set to scan continuously, or at a selectable interval and may include an alarm 1404 which may be visible, audible, or combinations of the same when an avalanche hazard (e.g., strong over weak layer) is detected and allow the vehicle 1400 operator to change course or stop travelling to avoid the hazard. As will be apparent to those of ordinary skill in the art having the benefit of this disclosure, the sensitivity, alarm triggers, scanning period, and the like, of the analyzer 100 may be user-configurable.

Although various embodiments have been shown and described, the present disclosure is not so limited and will be understood to include all such modifications and variations would be apparent to one skilled in the art.

What is claimed is:

1. A handheld device for detecting unstable hard-over-soft layers of snowpack comprising:
    a housing at least partially enclosing and holding at least components (a), (b), and (c) below;
    (a) an impulse radar chipset in communication with an antenna;
    (b) a display; and
    (c) at least one hardware processor programmed to perform a predefined set of operations at least a portion of which are stored in at least one memory, the predefined set of operations comprising:
    operating the impulse radar chipset and antenna to perform a radar scan and collect radar scan data for a portion of a snowpack;
    analyze the radar scan data to create a profile of snow depth and hardness; and
    displaying on the display the profile including an indicator for hard-over-soft layers that are layers of concern for instability.

2. The handheld device for detecting unstable hard-over-soft layers of snowpack of claim 1 further comprising:
    a position detection circuit; and
    wherein the predefined set of operations comprises:
    operating the position detection circuit to determine a current location on the Earth; and
    storing the current location with the profile of snow depth and hardness.

3. The handheld device for detecting unstable hard-over-soft layers of snowpack of claim 2 wherein the position detection circuit comprises a Global Positioning System (GPS).

4. The handheld device for detecting unstable hard-over-soft layers of snowpack of claim 1 further comprising:
    an inclinometer; and wherein the predefined set of operations comprises:
    operating the inclinometer to determine an inclination of a longitudinal axis of the handheld snowpack analyzer.

5. The handheld device for detecting unstable hard-over-soft layers of snowpack of claim 1 further comprising:
    a compass; and wherein the predefined set of operations comprises:
    operating the compass to determine a compass direction of a longitudinal axis of the handheld snowpack analyzer.

6. The handheld device for detecting unstable hard-over-soft layers of snowpack of claim 1 wherein the predefined set of operations
    converts the dielectric constant of snow layers to density, which is then converted to the HHT scale.

7. A vehicle mounted device for detecting unstable hard-over-soft layers of snowpack, the device comprising:
    a housing at least partially enclosing and holding at least components (a), (b), and (c) below;
    (a) an impulse radar chipset in communication with an antenna;
    (b) a display; and
    (c) at least one hardware processor programmed to perform a predefined set of operations at least a portion of which are stored in at least one memory, the predefined set of operations comprising:
    operating the impulse radar chipset and antenna to perform a radar scan and collect radar scan data for a portion of a snowpack;
    analyze the radar scan data to create a profile of snow depth and hardness; and
    providing on the display an indicator for hard-over-soft layers that are layers of concern for instability.

8. The vehicle mounted device for detecting unstable hard-over-soft layers of snowpack of claim 7 further comprising:
    a position detection circuit; and
    wherein the predefined set of operations comprises:
    operating the position detection circuit to determine a current location on the Earth; and
    storing the current location with the profile of snow depth and hardness.

9. The vehicle mounted device for detecting unstable hard-over-soft layers of snowpack of claim 8 wherein the position detection circuit comprises a Global Positioning System (GPS).

10. The vehicle mounted device for detecting unstable hard-over-soft layers of snowpack of claim 7 wherein the at least one hardware processor programmed to perform a predefined set of operations comprises a predefined set of operations that converts the dielectric constant of snow layers to density, which is then converted to the HET scale.

11. The vehicle mounted device for detecting unstable hard-over-soft layers of snowpack analyzer of claim 7 wherein the device is mounted to a_vehicle that comprises an unmanned remotely pilotable aircraft.

12. The vehicle mounted device for detecting unstable hard-over-soft layers of snowpack of claim 7 wherein the device is mounted to a vehicle that comprises a snowmachine and the device further comprises:

an alarm to indicate a potential avalanche condition.

* * * * *

UNITED STATES PATENT AND TRADEMARK OFFICE
CERTIFICATE OF CORRECTION

PATENT NO. : 11,131,613 B2  
APPLICATION NO. : 16/685808  
DATED : September 28, 2021  
INVENTOR(S) : Pratt et al.

Page 1 of 1

It is certified that error appears in the above-identified patent and that said Letters Patent is hereby corrected as shown below:

In the Claims

Column 10, Line 60, Claim 10 should read:
10. The vehicle mounted device for detecting unstable hard-over-soft layers of snowpack of claim 9 wherein the at least one hardware processor programmed to perform a predefined set of operations comprises a predefined set of operations that converts the dielectric constant of snow layers to density, which is then converted to the HHT scale.

Signed and Sealed this  
Eighth Day of February, 2022

Drew Hirshfeld  
*Performing the Functions and Duties of the*  
*Under Secretary of Commerce for Intellectual Property and*  
*Director of the United States Patent and Trademark Office*